United States Patent [19]

Namiki et al.

[11] Patent Number: 4,840,937
[45] Date of Patent: Jun. 20, 1989

[54] SURFACTANT COMPOSED OF ACYLATED COLLAGEN OR ACYLATED GELATINE AND A PRODUCTION PROCESS THEREOF

[75] Inventors: Tetsuro Namiki, Ome; Masayasu Furuse, Sagamihara; Yoshimitsu Kuroyanagi, Hachiogi; Teruo Miyata, Tokyo; Takashi Suzuki, Yokohama, all of Japan

[73] Assignees: Koken Co., Ltd.; Shiseido Co., Ltd., both of Tokyo, Japan

[21] Appl. No.: 97,400

[22] Filed: Sep. 16, 1987

Related U.S. Application Data

[63] Continuation of Ser. No. 845,442, Mar. 28, 1986, abandoned.

[30] Foreign Application Priority Data

Apr. 6, 1985 [JP] Japan .................................. 60-71896

[51] Int. Cl.$^4$ .......................... C08H 1/06; C08L 89/04; C08L 89/06
[52] U.S. Cl. .................... 514/21; 252/356; 424/70; 514/773; 530/354; 530/356
[58] Field of Search ............... 530/354, 356, 416, 417; 514/21, 773; 252/356; 424/70

[56] References Cited

U.S. PATENT DOCUMENTS

| | | | |
|---|---|---|---|
| 2,015,912 | 10/1935 | Sommer | 530/354 X |
| 2,119,872 | 6/1938 | Wiegand | 530/354 X |
| 2,164,284 | 6/1939 | Ralston et al. | 530/356 X |
| 2,363,892 | 11/1944 | Monier | 530/354 |
| 2,794,796 | 6/1957 | Cavanaugh | 530/354 |
| 3,138,581 | 6/1964 | Young et al. | 530/354 X |
| 3,628,974 | 12/1971 | Battista | 530/356 X |
| 3,712,865 | 1/1973 | Evans et al. | 530/354 X |
| 3,954,725 | 5/1976 | Johnsen et al. | 424/70 X |
| 3,985,722 | 10/1976 | Yoshida et al. | 530/354 X |
| 3,988,438 | 10/1976 | Weinstein | 514/773 |
| 3,991,184 | 11/1976 | Kludas et al. | 514/21 |
| 4,076,800 | 2/1978 | Marsh et al. | 514/773 X |
| 4,140,537 | 2/1979 | Luck et al. | 530/356 X |
| 4,215,200 | 7/1980 | Miyata et al. | 530/356 X |
| 4,223,984 | 9/1980 | Miyata et al. | 530/356 X |
| 4,234,475 | 11/1980 | Sokol | 530/354 X |
| 4,260,228 | 4/1981 | Miyata | 530/356 |
| 4,268,131 | 5/1981 | Miyata et al. | 530/356 V |
| 4,271,070 | 6/1981 | Miyata et al. | 530/356 |
| 4,406,833 | 9/1983 | Boehme et al. | 530/354 X |
| 4,424,208 | 1/1984 | Wallace et al. | 530/356 X |
| 4,451,385 | 5/1984 | Tauss et al. | 514/773 X |
| 4,557,764 | 12/1985 | Chu | 530/356 X |
| 4,565,580 | 1/1986 | Miyata et al. | 530/356 X |
| 4,582,640 | 4/1986 | Smestad et al. | 530/356 |
| 4,592,864 | 6/1986 | Miyata et al. | 530/356 |
| 4,705,682 | 11/1987 | Moeller et al. | 252/356 X |
| 4,714,758 | 12/1987 | Namiki et al. | 530/354 |
| 4,784,986 | 11/1988 | Usher | 514/21 X |

*Primary Examiner*—Howard E. Schain
*Attorney, Agent, or Firm*—Sherman and Shalloway

[57] ABSTRACT

This invention relates to a surfactant with less toxicity and irritation against the human body and a production process thereof. The surfactant is produced by the acylation of the side chain amino radicals of collagen or gelatine with an aliphatic acid having 2 to 26 carbon atoms; it is used as an emulsifier and an antiseptic for cosmetics.

4 Claims, No Drawings ized especially in the carbon numbers from 2 to 26.
SURFACTANT COMPOSED OF ACYLATED COLLAGEN OR ACYLATED GELATINE AND A PRODUCTION PROCESS THEREOF This application is a continuation of application Ser. No. 845,442, filed Mar. 28, 1986, now abandoned.

FIELD OF THE INVENTION

This invention relates to a surfactant; more particularly, this invention relates to a surfactant with less toxicity and irritation especially against the human body, which is, therefore, useful as an emulsifier or an antiseptic for cosmetics and a production process thereof.

DESCRIPTION OF THE PRIOR ART

Nowadays surfactants are widely used in various industrial fields and their variety is numerous indeed. However, as their use is on the increase, there have appeared problems with their effects on the human body and on the environment by virtue of their pollutional effect. Their safety has thus become a very important factor in addition to their effectiveness; especially, in cosmetic and foodstuff industries the safety to the human body is required. Meanwhile, recently, surfactants causing less roughening of hands have been put on the market in the cosmetic field, but in terms of toxicity and irritation, there are very few which are satisfactory.

SUMMARY OF THE INVENTION

Under the circumstances, the present inventors have made various studies in search for a biologically decomposable surfactant with less toxicity and irritation and finally accomplished the invention. That is, the invention concerns a surfactant composed of acylated collagen or acylated gelatine produced by the acylation of the side chain amino radicals of collagen or gelatine with an aliphatic acid having 2 to 26 carbon atoms.

DETAILED DESCRIPTION OF THE INVENTION

The inventors made various attempts based on the thought that since collagen is a constituent of living bodies, gelatine is a heat-denatured product of collagen and most of aliphatic acids are also derived from organisms, it might be possible to produce a biologically decomposable surfactant safe to the human body by the employment of the above substances as reactants and this led them to the accomplishment of the invention. The surfactant of this invention is composed of collagen or gelatine whose side chain amino radicals are chemically modified by the acylation with an aliphatic acid having 2 to 26 carbon atoms. That is, it can be produced on a commercial scale by subjecting collagen or gelatine to the acylation reaction in association with an aliphatic acid with 2–26 carbon atoms.

In an embodiment of this, an anhydride of the aliphatic acid is added to a collagen or gelatine solution at 25° C. and below with stirring after the pH of the solution is adjusted to 8–14 in order to acylate amino radicals on the side chain of the collagen or the gelatine molecule. As seen from this, various surfactants different in the surface active power can be produced in this invention in compliance with different sorts of aliphatic acids and variations in the amino radical modification degree therewith.

In regard to the aliphatic acids, the surfactant becomes more oleophilic with the increase of their carbon number; a remarkable surface active power can be recognized especially in the carbon numbers from 2 to 26. In contrast to the above, the surfactant becomes more hydrophilic with the decrease of the amino radical modification degree. Generally, a slight difference can be perceived in the surface active power as to the variation in the aliphatic acid carbon number, but a striking surface active power appears in the amino radical modification degree from 5 to 50%. Particularly, the most suitable surface active power is given when the amino radical modification degree is about 20%.

In this invention, any functional derivatives of the aliphatic acid, such as anhydride, chloride and so forth, may be used to acylate the side chain amino radicals of collagen or gelatine, but anhydride is the most desirable of all in view of the susceptibility to reaction.

This invention will be understood more readily in reference to the following examples; however, these examples are intended to illustrate the invention and are not to be construed to limit the scope of the invention.

EXAMPLE 1

Fifteen grams of atelocollagen (containing about 0.006 mole of $\epsilon$-$NH_2$) was dissolved in 500 ml of water at pH 3. Thereafter, the pH of the solution was adjusted to 13 by the use of a NaOH aqueous solution. Twenty milliliters of tetrahydrofuran mixed with 0.006 mole of heptanoic acid anhydride were added to the alkaline atelocollagen aqueous solution gradually. The acylation reaction was conducted at room temperatures at 25° C. and below for 3 hours with stirring. After the reaction, with the pH kept at 13 1,000 ml of ethanol were added thereto to precipitate a product resulting from the reaction. The precipitated product was filtered out and then put to another three cycles of filtration with ethanol containing a trace of hydrochloric acid (0.03 mole) in order to eliminate heptanoic acid having not yet reacted with collagen. The reason for using a trace of HCl is to convert sodium aliphatate, a decomposition by-product of heptanoic acid anhydride, into the former aliphatic acid that dissolves in ethanol readily.

After enough rinsing, ethanol was removed from the product, which was then suspended in water and rendered a creamy product by means of a homogenizer. At this moment, the collagen consistency was 4%, the pH was 6 and the amino radical modification degree was found to be in the range 20–30%.

When two times or three times as much heptanoic acid anhydride as $\epsilon$-$NH_2$ radicals of the lysine residue of the collagen molecule was added to the alkaline atelocollagen aqueous solution, the amino radical modification degree became 30–40% and 35–40% in correspondence therewith. An acid-soluble collagen and a salt-soluble collagen were used individually in place of atelocollagen, but their result was similar to the above.

EXAMPLE 2

Fifteen grams of gelatine (containing about 0.006 mole of $\epsilon$-$NH_2$) was dissolved in water with heating. The pH of the solution was adjusted to 13. Twenty milliliters of tetrahydrofuran mixed with 0.006 mole of heptanoic acid anhydride were added thereto. An acylated product was yielded by the same procedure as in Example 1. The amino radical modification degree of the product was in the range 20–35%.

EXAMPLE 3

Myristic acid (=tetradecanoic acid: $CH_3(CH_2)_{12}COOH$) was dissolved in 20 ml of tetrahydrofuran and added thereto was 0.01 mole of triethylamine. The mixture solution was cooled to 5° C. to −10° C., to which 0.012 mole of ethyl chlorocarbonate was added with stirring. The reacted solution was filtered; the filtrate was evaporated and dried. By the use of a dried residue in place of heptanoic acid anhydride used in Examples 1 and 2, acylated collagen and acylated gelatine of amino radical modification degree 30–50% were obtained by the same operational procedure as in Examples 1 and 2.

EXAMPLE 4

Mixtures composed of water and olive oil in arbitrary proportion were emulsified by the use of acylated collagen and acylated gelatine suspension produced in Examples 1, 2 and 3 respectively. As a result, emulsions with good dispersion were obtained.

As stated above, according to the invention, a surfactant superior to conventional ones in surface active power and having less toxicity and irritation can be produced from collagen, a constituent of living bodies, or gelatine, a heat-denatured product of collagen, by the acylation with an aliphatic acid. The surfactant can be employed for numerous industries including cosmetics and foodstuffs. Also, it provides a good effect especially suitable for manufacturing cosmetics.

What is claimed is:

1. A non-irritating cosmetic composition for application to the human body comprising an emulsion of water, a cosmetically acceptable oily material, and as an emulsifier, a surfactant comprising an acylated atelocollagen which is the reaction product between atelocollagen and an aliphatic acid having from 2 to 26 carbon atoms or an anhydride thereof reacted at a temperature of about 25° C. or lower and at a pH in the range of from 8 to 14.

2. The non-irritating cosmetic composition of claim 1 wherein the reaction between atelocollagen and said aliphatic acid or anhydride thereof is carried out until about 20% of the side chain amino radicals of atelocollagen are acylated with said aliphatic acid or anhydride thereof.

3. The non-irritating cosmetic composition of claim 1 wherein the aliphatic acid is myristic acid.

4. The non-irritating cosmetic composition of claim 1 wherein the aliphatic acid is heptanoic acid anhydride.

* * * * *